(12) United States Patent
Hite et al.

(10) Patent No.: US 12,128,054 B2
(45) Date of Patent: Oct. 29, 2024

(54) AQUEOUS PHARMACEUTICAL COMPOSITIONS OF PROSTAGLANDINS

(71) Applicant: FAMYGEN LIFE SCIENCES, INC., Framingham, MA (US)

(72) Inventors: William Hite, Winchester, CA (US); Nilesh Parikh, Irvine, CA (US)

(73) Assignee: FAMYGEN LIFE SCIENCES, INC., Framingham, MA (US)

( * ) Notice: Subject to any disclaimer, the term of this patent is extended or adjusted under 35 U.S.C. 154(b) by 0 days.

(21) Appl. No.: 18/049,952

(22) Filed: Oct. 26, 2022

(65) Prior Publication Data

US 2024/0156833 A1   May 16, 2024

(51) Int. Cl.
| | |
|---|---|
| A61K 31/5575 | (2006.01) |
| A61K 9/00 | (2006.01) |
| A61K 47/02 | (2006.01) |
| A61K 47/12 | (2006.01) |
| A61K 47/18 | (2017.01) |

(52) U.S. Cl.
CPC ........ *A61K 31/5575* (2013.01); *A61K 9/0048* (2013.01); *A61K 47/02* (2013.01); *A61K 47/12* (2013.01); *A61K 47/183* (2013.01)

(58) Field of Classification Search
None
See application file for complete search history.

(56) References Cited

U.S. PATENT DOCUMENTS

| | | |
|---|---|---|
| 7,795,316 B1 | 9/2010 | Kabra |
| 8,586,630 B2 | 11/2013 | Chan et al. |
| 9,155,716 B2 | 10/2015 | Chang et al. |
| 2021/0177863 A1* | 6/2021 | Shah .................... A61K 31/165 |
| 2022/0125801 A1 | 4/2022 | Chaurasia et al. |

FOREIGN PATENT DOCUMENTS

| | | | | |
|---|---|---|---|---|
| WO | WO-2018185788 A1 * | 10/2018 | ......... | A61K 31/5575 |
| WO | 2021084522 | 5/2021 | | |

OTHER PUBLICATIONS

Labib, "The Purpose of Prostaglandins", 2018, Review of Optometery, pp. 1-4 (Year: 2018).*
Junemann et al., "Drug bioavailability from topically applied ocular drops. Does drop size matter?", 2016, Opthalmology Journal, 1, pp. 29-35 (Year: 2016).*
Baudouin et al., "Preservatives in eyedrops: The good, the bad and the ugly", 2010, Progress in Retinal and Eye Research, 29, pp. 312-334 (Year: 2010).*
Müller-Lierheim. "Hylan A: A Novel Transporter for Latanoprost in the Treatment of Ocular Hypertension," Biomed. J. Sci. Tech. Res., vol. 37(1), pp. 29176-81 (2021).
Hahne et al., "Prevalidation of a Human Cornea Construct as an Alternative to Animal Corneas for In Vitro Drug Absorption Studies," J. Pharm. Sci., vol. 101, pp. 1976-1988 (2012).
Hippalganokar, "Biopharmaceutical approaches for improved drug delivery across ocular barriers," University of Mississippi, Electronic Theses and Dissertations, 1484 (2011), 270 pages.
Allergan, Inc. "Product Monograph: PrLumigan RC(R) Bimatoprost Ophthalmic Solution 0.01% w/v," Submission Control No. 218812 (Nov. 26, 2018).
Ellis (Reviewer), Pharmacology/Toxicology Review and Evaluation, Bimatoprost Ophthalmic Solution 0.01% (Mar. 21, 2008).
Hopes et al., "Preservative-free Treatment in Glaucoma is Sensible and Realistic Aim for the Future," Eur. Ophthalmic Rev., vol. 4, pp. 23-28 (2010).
Gote et al., "Prodrugs and nanomicelles to overcome ocular barriers for drug penetration," Expert Op. Drug Metab. & Tox., accepted manuscript posted online Jul. 30, 2020, 46 pages.
Kompella et al., "Recent advances in ophthalmic drug delivery," Ther. Deliv., vol. 1(3), pp. 435-456 (2010).
Kabashima et al., "Effects of Benzalkonium Chloride and Preservative-Free Composition on the Corneal Epithelium Cells," J. Ocular Pharm. Ther., published online at https://www.liebertpub.com/doi/full/10.1089/jop.2019.0165 (2020).
Bertens et al., "Topical drug delivery devices: A review," Exp. Eye Res., vol. 168, pp. 149-160 (2018).
Ghate et al., "Barriers to Glaucoma Drug Delivery," J. Glaucoma, vol. 17(2), pp. 147-156 (Mar. 2008).
Campos et al., "The prominence of the dosage form design to treat ocular diseases," Int. J. Pharm (2020).
Baudoin et al., "Preservatives in eye drops: The good, the bad and the ugly," Prog. Ret. Eye Res., vol. 29, pp. 312-334 (2010).
Achouri et al., "Recent advances in ocular drug delivery," Drug. Dev. Indus. Pharm. (2012).
Marsh et al., "The Influence of Non-ionic Detergents and Other Surfactants on Human Corneal Permeability," Exp. Eye Res., vol. 11, pp. 43-48 (1971).
Wroblewska et al., "Progress in drug formulation design and delivery of medicinal substances used in ophthalmology," Int. J. Pharm., vol. 607, pp. 121012 (2021).
Kirihara et al., "Pharmacologic Characterization of Omidenepag Isopropyl, a Novel Selective EP2 Receptor Agonist, as an Ocular Hypotensive Agent," Invest. Ophthalmol. Vis. Sci., vol. 59, pp. 145-153 (2018).

(Continued)

*Primary Examiner* — Jeffrey H Murray
*Assistant Examiner* — Madeline E Braun
(74) *Attorney, Agent, or Firm* — ArentFox Schiff LLP

(57) ABSTRACT

Aqueous pharmaceutical compositions, suitable for topical ophthalmic administration to a mammal, that comprise a therapeutically effective amount of a prostaglandin, less than 0.3% w/v, and no added benzalkonium chloride, are provided. Such compositions are useful in methods comprising their topical administration to mammalian subjects, e.g., humans and reducing intraocular pressure and/or ocular hyperemia in the patient. Such compositions are also useful in methods comprising their topical administration to mammalian subjects, e.g., humans and promoting eyelash growth in the patient.

10 Claims, No Drawings

(56) References Cited

OTHER PUBLICATIONS

Mahaling et al., "Understanding the influence of surface properties of nanoparticles and penetration enhancers for improving bioavailability in eye tissues in vivo," Int. J. Pharm. (2016).

Gote et al., "Ocular Drug Delivery: Present Innovations and Future Challenges," J. Pharm. Exp. Ther., vol. 370(3), pp. 602-624 (2019).

Kikuchi et al., "Synergistic effect of EDTA and boric acid on corneal penetration of CS-088," Int. J. Pharm., vol. 290, pp. 83-89 (2005).

Lee, "Mechanisms and Facilitation of Corneal Drug Penetration," J. Controlled Release, vol. 11, pp. 79-90 (1990).

Sasaki et al., "Different effects of absorption promoters on corneal and conjunctival penetration of ophthalmic beta-blockers," Pharm. Res., vol. 12(8), pp. 1146-1150 (1995).

Thakrhal et al., "EDTA decreases in vitro transcorneal permeation of fluconazole in phosphate buffer through excised sheep cornea," J. Pharm. Neg. Res., vol. 2(1), pp. 24-27 (2011).

Moiseev et al., "Penetration Enhancers in Ocular Drug Delivery," Pharmaceutics, vol. 11, p. 321 (2019).

Ahuja et al., "Effect of Formulation Parameters on Corneal Permeability of Ofloxacin," Sci. Pharm., vol. 76, pp. 505-514 (2008).

Mohanty et al., "Effect of formulation factors on in vitro transcorneal permeation of voriconazole from aqueous drops," J. Adv. Pharm. Technol. Res., vol. 4(4), pp. 210-216 (2018).

Pawar et al., "Effect of formulation factors on in vitro permeation of moxifloxacin from aqueous drops through excised goat, sheep, and buffalo corneas," AAPS Pharm. Sci. Tech., vol. 7, No. E89 (2006).

Ashton et al., "Location of penetration and metabolic barriers to levobunolol in the corneal epithelium of the pigmented rabbit," J. Pharm. Exp. Ther., vol. 259(2), pp. 719-724 (1991).

Pescina et al., Eur J Pharm Biopharm, 107:171-179 (2016).

Grass et al. Investig Ophthalmol Vis Sci, 26: 110-113 (1985).

\* cited by examiner

AQUEOUS PHARMACEUTICAL COMPOSITIONS OF PROSTAGLANDINS

FIELD

This application provides aqueous, pharmaceutical compositions, suitable for topical, ophthalmic administration, comprising bimatoprost and ethylenediaminetetraacetic acid ("EDTA") and/or xanthan gum, and methods of making and using same.

BACKGROUND

Bimatoprost is a well-characterized active agent useful to reduce intraocular pressure (TOP). Bimatoprost has an empirical formula of $C_{25}H_{37}NO_4$, a molecular weight of 415.57 g/mol and a structural formula, of its clinically important isomer, as shown:

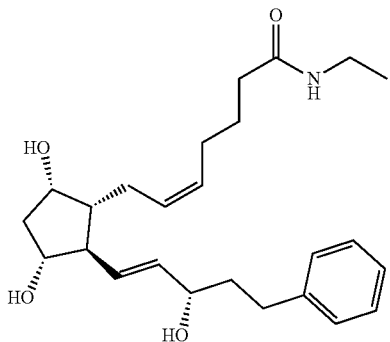 [SMILES: CCNC(=O)CCC/C=C\C[C@@H]1[C@@H](/C=C/[C@@H](O)CCc2ccccc2)[C@H](O)C[C@@H]1O]

Bimatoprost is alternatively known by its IUPAC name (5Z)-7-[(1R,2R,3R,5S)-3,5-dihydroxy-2-[(1E,3S)-3-hydroxy-5-phenyl-1-penten-1-yl]cyclopentyl]-N-ethyl-5-heptenamide, and by its CAS Registry Number 155206-00-1.

In vivo, bimatoprost is hydrolyzed to its biologically-active, free-acid form, bimatoprost acid having a structural formula as shown:

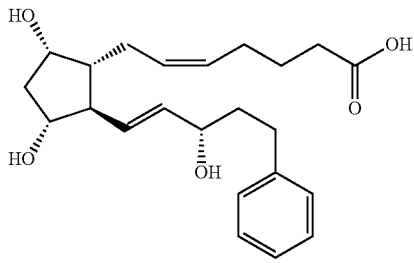 [SMILES: O=C(O)CCC/C=C\C[C@@H]1[C@@H](/C=C/[C@@H](O)CCc2ccccc2)[C@H](O)C[C@@H]1O]

Currently, bimatoprost is the main active component in commercial formulations provided under the trade names LUMIGAN® (0.01% ophthalmic solution, Allergan) and LATISSE® (0.03% ophthalmic solution, AbbVie). Both formulations contain the cationic detergent, benzalkonium chloride. And, at least in the case of LUMIGAN®, two hundred parts per million benzalkonium chloride is included as a tissue penetration enhancer for the 0.01% w/v bimatoprost topical, ophthalmic formulations, promoting its flux across and/or into ophthalmic tissues and structures such as corneal epithelium and aqueous humor. (See, e.g., U.S. Pat. No. 9,155,716, Orange Book listed for LUMIGAN® at the time the present disclosure was filed.)

WO2021/084522 teaches that it is possible to formulate bimatoprost in 0.01% eye drops with no more than 80 ppm of benzalkonium chloride, while obtaining a bioavailability comparable with that of LUMIGAN® 0.1% if a poloxamer, or a mixture of several different poloxamers, is added to the composition. WO2021/084522 teaches that the overall poloxamer concentration must be between 0.005% w/v and 0.1% w/v to achieve equivalent bioavailability to LUMIGAN® 0.1%. Optionally, poloxamer may be in combination with 0.05-0.15% w/v EDTA and/or in combination with 0.01-0.15% w/v polysorbate or TWEEN (respectively, common and commercial name of ethoxylated sorbitan esters), such as polysorbate 20 or polysorbate 80. The addition of these additional agents will further improve the corneal permeability of bimatoprost. WO2021/084522 teaches that EDTA is a stabilizing agent that could be useful to reduce the oxidative degradation that can be accelerated by the presence of metallic impurities.

U.S. Pat. No. 7,795,316 (the "316 patent") teaches aqueous suspensions of tobramycin and dexamethasone that are suitable for topical-ophthalmic administration. The 316 patent taught suspensions contain xanthan gum and ionic species, in amounts that are sufficient to limit interactions between tobramycin and xanthan gum, so that no precipitates or clumps of tobramycin and xanthan gum are formed, and that are sufficient to result in the viscosity of the suspensions not being elevated above 700 centipoises. The 316 patent teaches that the xanthan gum used in its aqueous suspensions must be deacetylated so that the viscosity of those suspension are stable for a period of 18 months after their manufacture. The aqueous suspensions have a pH in the range of 5 to 6.

The 316 patent teaches that pharmaceutical grade xanthan gum should be utilized and explains the importance of deacetylating xanthan gum in its Examples 1 and 2. Also in Example 2, the 316 patent teaches the following method for deacetylating xanthan gum: Xanthan gum was weighed and slowly added to water in a vessel while mixing. 2.5 ml of 1 N NaOH or equivalent per 1 g of xanthan gum was added and mixed for 20 minutes. 1.66 ml of 1N HCl or equivalent per 1 g of xanthan gum was then added. Purified water was added to adjust to the target weight, followed by mixing for 15 minutes. The deacetylated xanthan gum was then filtered through an appropriate filter e.g., a 1.2 μm filter. Example 1 of the 316 patent discloses the preparation of formulations comprising tobramycin, dexamethasone, and xanthan gum that has not been deacetylated. The ingredients of those formulations and their viscosities are reported in Table 1A (reproduced below). As can be seen, the Table 1A formulations 107201 and 107209 have a high degree of qualitative and quantitative relatedness. They differ in only three ways. The former comprises more sodium chloride and has a lower pH than the latter. The former is pH adjusted with hydrochloric acid whereas the latter is pH adjusted with sulfuric acid. And the former has a lower viscosity than the latter.

TABLE 1A

| | Formulation Number | |
|---|---|---|
| | 107201 W/V % | 107209 W/V % |
| INGREDIENTS | | |
| Tobramycin | 0.3 | 0.3 |
| Dexamethasone | 0.1 | 0.1 |
| Xanthan Gum | 0.9 | 0.9 |

TABLE 1A-continued

|  | Formulation Number | |
| --- | --- | --- |
|  | 107201 W/V % | 107209 W/V % |
| Sodium chloride | 0.42 | 0.08 |
| Tyloxapol | 0.05 | 0.05 |
| Boric Acid | 0.5 | 1 |
| Disodium Edetate | 0.01 | 0.01 |
| Sodium Hydroxide | Adjust pH to 5.5 | Adjust pH to 5.7 |
| Hydrochloric Acid | Adjust pH to 5.5 | None |
| Sulfuric Acid | None | Adjust pH to 5.7 |
| Purified Water | Qs to 100% | Qs to 100% |
| RESULTS |  |  |
| Viscosity at shear rate 6 sec−1 (cps) | 418 | 642 |

Example 1 of the 316 patent discloses that the formulations described in its Table 1A were subjected to accelerated stability testing and reported in Table 1B (reproduced below). The 316 patent states its Table 1B shows the pH and viscosities of the Table 1A formulations, which were prepared using xanthan gum that has not been deacetylated, decrease upon storage. This eventually makes the formulations unstable. Specifically, the uniform nature of the suspensions was lost.

TABLE 1B

Stability of pH and Viscosity of Tobramycin/ Dexamethasone Formulation Prepared using Non-Deacetylated Xanthan Gum

|  | 107201 pH | 10729 | 107201 Viscosity of Formulation (cps) | 107209 |
| --- | --- | --- | --- | --- |
| Initial | 5.48 | 5.74 | 418 | 642 |
| 40° C., 4 Weeks | 5.33 | 5.56 | 187 | 217 |
| 40° C., 8 Weeks | 5.08 | 5.36 | 86 | 141 |
| 40° C., 16 Weeks | 4.86 | 4.89 | 25 | 37 |
| 50° C., 1 Week | 5.37 | 5.73 | 175 | 240 |
| 50° C., 2 Weeks | 5.20 | 5.25 | 95 | 160 |
| 50° C., 4 Weeks | 5.10 | 5.14 | 48 | 91 |
| 50° C., 8 Weeks | 4.70 | 4.81 | Not Uniform | Not Uniform |
| 60° C., 1 Week | 5.20 | 5.16 | 68 | 132 |
| 60° C., 2 Weeks | Not Uniform | 4.83 | Not Uniform | 43 |
| 60° C., 4 Weeks | Not Uniform | Not Uniform | Not Uniform | Not Uniform |

Example 2 of the 316 patent discloses the preparation of a formulation comprising tobramycin, dexamethasone, and xanthan gum that has been deacetylated. The ingredients of that formulation, 108536, and its viscosity are reported in Table 2A (reproduced below). As can be seen, the Table 2A formulation differs qualitatively from the 107201 and 107209 formulations by containing propylene glycol, sodium sulfate, and benzalkonium chloride and by lacking boric acid and sulfuric acid (as compared to formulation 101209 only). The 108536 formulation differs quantitatively from the 107201 and 107209 formulations by having and an intermediate pH and amount of sodium chloride and a lower amount of xanthan gum. The 108536 formulation has the same amount of tobramycin, dexamethasone, tyloxapol, and disodium edetate as the 107201 and 107209 formulations.

TABLE 2A

|  | Formulation Number 108536 W/V % |
| --- | --- |
| INGREDIENTS |  |
| Tobramycin | 0.3 |
| Dexamethasone | 0.1 |
| Xanthan Gum | 0.6 |
| Sodium chloride | 0.24 |
| Propylene Glycol | 0.6 |
| Tyloxapol | 0.05 |
| Sodium Sulfate (Anhydrous) | 0.25 |
| Disodium Edetate | 0.01 |
| Benzalkonium Chloride | 0.01 |
| Sodium Hydroxide | Adjust pH to 5.75 |
| Hydrochloric Acid | Adjust pH to 5.75 |
| Purified Water | Qs to 100% |
| RESULTS |  |
| Viscosity at shear rate 6 sec−1 (cps) | 116 |
| Simulated In Vivo Viscosity at shear rate 6 sec−1 (cps) | 1059 |
| Viscosity of Formulation as a % of Simulated In Vivo Viscosity | 11% |

Example 2 of the 316 patent discloses that the formulation described in its Table 2A was subjected to accelerated stability testing and reported in Table 2B (reproduced below). The 316 patent states that its Table 2B shows the pH values of the Table 2A formulation, which were prepared using xanthan gum that has been deacetylated, unlike the 107201 and 107209 formulations. The 316 patent states that, as a result, the viscosity of the 108536 formulation remained stable or increased during storage, rather than decreasing as did the 107201 and 107209 formulations.

TABLE 2B

Stability of pH and Viscosity of Tobramycin/Dexamethasone Formulations Prepared Using Deacetylated (Pre-treated) Xanthan Gun

|  | Formulation Number 108536 | |
| --- | --- | --- |
| Analysis | pH | Pre-dose Viscosity (cps) |
| Initial | 5.84 | 116 |
| 40° C., 4 Weeks | 5.80 | 166 |
| 40° C., 8 Weeks | 5.81 | 167 |
| 40° C., 12 Weeks | 5.81 | 181 |
| 40° C., 16 Weeks | ND | ND |
| 40° C., 26 Weeks | ND | ND |
| 50° C., 1 Week | 5.79 | ND |
| 50° C., 2 Weeks | 5.78 | 152 |
| 50° C., 4 Weeks | 5.76 | 179 |
| 50° C., 8 Weeks | 5.73 | 271372 |
| 50° C., 16 Weeks | ND | NA |
| 60° C., 1 Week | 5.79 | 150 |
| 60° C., 2 Weeks | 5.78 | 172 |
| 60° C., 3 Weeks | ND | ND |
| 60° C., 4 Weeks | 5.66 | 235 |

ND = Not Determined

SUMMARY OF VARIOUS EMBODIMENTS

The present disclosure provides aqueous pharmaceutical compositions, suitable for topical-ophthalmic administration, that consist of, consist essentially of, or comprise from 0.001% w/v to 2% w/v of a prostaglandin that is bimatoprost, latanoprost, tafluprost, travoprost, unoprostone, a derivative thereof or combinations thereof; from 0.0025% w/v to 0.25% w/v of an ocular tissue penetration enhancer that is EDTA, ethylene glycol tetraacetic acid ("EGTA"), ethylenediamine-N,N'-disuccinic acid ("EDDS"), or a combination thereof; from 0.001% w/v to 2% w/v of an ionic tonicity agent that is calcium chloride, magnesium chloride, potassium chloride, sodium chloride, sodium sulfate, or a combination thereof. Such compositions have an osmolality of from 250 milliosmoles ("mOsm") to 350 mOsm; a viscosity of from 1 centipoise ("cps") to 8000 cps; and are free of added benzalkonium chloride. In some embodiments, the compositions are free of added: (i) benzalkonium chloride, and (ii) poloxamer. In some embodiments, the compositions are free of added: (i) benzalkonium chloride, (ii) poloxamer, and (iii) polysorbate.

The topical, ophthalmic compositions of the present disclosure may further comprise a buffer that is tris(hydroxymethyl)aminomethane ("TRIS"), acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, a tartaric acid, a sodium tartrate, a sodium bicarbonate, a sodium carbonate, or a combination thereof; and a pH adjusting agent that is sodium hydroxide, potassium hydroxide, citric acid, hydrochloric acid, or a combination thereof. In such compositions, the buffer and pH adjusting agent are present in the composition in amounts sufficient to cause the composition to have a pH of from 5 to 9.

In some compositions of the present disclosure, the prostaglandin is bimatoprost and the penetration enhancer is EDTA. In some such compositions, the bimatoprost is present therein in an amount of from 0.01% w/v to 0.03% w/v. In some such compositions, the EDTA is present therein in an amount from 0.05% w/v to 0.15% w/v.

In some compositions of the present disclosure, the ionic tonicity agent is sodium chloride, the buffer is the combination of dibasic sodium phosphate and citric acid; and the pH adjusting agent is hydrochloric acid. In some such compositions, the bimatoprost is present therein in the amount of 0.01% w/v, the EDTA is present therein in the amount of 0.1% w/v, the sodium chloride is present therein in an amount of from 0.75% w/v to 0.85%; the dibasic sodium phosphate is present therein in an amount of from 0.25% w/v to 0.275% w/v; and the citric acid is present therein in an amount of from 0.0125% w/v to 0.175% w/v. Such compositions further have a pH of from 6 to 8.

In certain embodiments, the aqueous pharmaceutical compositions of the present disclosure are "substantially free of quaternary ammonium salt." As applied to such a composition, "substantially free of quaternary ammonium salt" means that the composition does not contain any more than trace amounts of quaternary ammonium salt that might be introduced into the composition by way of its existence in the various components or excipients of the composition as a consequence, or byproduct, of their processes of manufacture or by way of the process of manufacture of the composition itself. In some embodiments, such substantially quaternary ammonium salt free compositions contain quaternary ammonium salt in an amount less than 25 PPM, less than 15 PPM, less than 10 PPM, less than 5 PPM, less than 1 PPM, less than 0.1 PPM, less than 0.01 PPM, or less than 0.001 PPM. In certain embodiments, the quaternary ammonium salt is methylbenzethonium chloride, benzalkonium chloride, cetalkonium chloride, cetrimonium sodium chloride, domiphen bromide, cetylpyridinium chloride, didecyldimethylammonium chloride, benzethonium chloride, benzoxonium chloride, polydronium chloride, tetraethylammonium bromide, or a combination thereof.

In certain embodiments, the aqueous pharmaceutical compositions of the present disclosure are substantially free of polymer(s) that undergo a phase transition from liquid to gel following topical administration to ocular tissues, referred to herein as "ophthalmic gelling polymer." As applied to such a composition, "substantially free of ophthalmic gelling polymer" means that the composition does not contain any more than trace amounts of ophthalmic gelling polymer that might be introduced into the composition by way of its existence in the various components or excipients of the composition as a consequence, or byproduct, of their processes of manufacture or by way of the process of manufacture of the composition itself. In some embodiments, such substantially ophthalmic gelling polymer free compositions contain ophthalmic gelling polymer in an amount less than 0.0025% w/v, less than 0.001% w/v, less than 0.00075% w/v, less than 0.0005% w/v, less than 0.00025% w/v, or less than 0.0001% w/v. In certain embodiments, the ophthalmic gelling polymer is a poloxamer, such as poloxamer 188, poloxamer 407, or a combination thereof.

In certain embodiments, the aqueous pharmaceutical compositions of the present disclosure are "substantially free of polysorbate." As applied to such a composition, "substantially free of polysorbate" means that the composition does not contain any more than trace amounts of polysorbate that might be introduced into the composition by way of its existence in the various components or excipients of the composition as a consequence, or byproduct, of their processes of manufacture or by way of the process of manufacture of the composition itself. In some embodiments, such substantially polysorbate free compositions contain polysorbate in an amount less than 0.01% w/v, less than 0.0075% w/v, less than 0.005% w/v, less than 0.0025% w/v, less than 0.001% w/v, less than 0.00075% w/v, less than 0.0005% w/v, less than 0.00025% w/v, less than 0.0001% w/v, less than 0.000075% w/v, less than 0.00005% w/v, or less than 0.00001% w/v. In certain embodiments, the polysorbate is polysorbate 20, polysorbate 80, or a combination thereof.

The present disclosure further provides aqueous pharmaceutical compositions that are suitable for topical-ophthalmic administration and that consist of, consist essentially of, or comprise from 0.001% w/v to 2% w/v of a prostaglandin that is bimatoprost, latanoprost, tafluprost, travoprost, unoprostone, or a combination thereof; from 0.0025% w/v to 0.25% w/v of an ocular tissue penetration enhancer that is EDTA, EGTA, EDDS, or a combination thereof; from 0.001% w/v to 2% w/v of an ionic tonicity agent that is a calcium chloride, a magnesium chloride, a potassium chloride, a sodium chloride, a sodium sulfate, or a combination thereof; and between 0.1% w/v and 1.5% w/v of a nondeacetylated xanthan gum. Such compositions have an osmolality of from 250 milliosmoles (mOsm) to 350 mOsm; a viscosity of from 1 centipoise ("cps") to 8000 cps; are free of added benzalkonium chloride; and are at least 70% viscosity stable for one week at 50° C. In some embodiments, the compositions are free of added benzalkonium chloride. In some embodiments, the compositions are free of added benzalkonium chloride and poloxamer.

The topical, ophthalmic compositions of the present disclosure may further comprise a buffer that is TRIS, acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, tartaric acid, sodium tartrate, sodium bicarbonate, sodium carbonate, or a combination thereof; a pH adjusting agent that is sodium hydroxide, potassium hydroxide, citric acid, hydrochloric acid, or a combination thereof. In such compositions, the buffer and pH adjusting agent are present in the composition in amounts sufficient to cause the composition to have a pH of from 5 to 9.

In some compositions of the present disclosure, the prostaglandin is bimatoprost and the penetration enhancer is EDTA. In some such compositions, the bimatoprost is present therein in an amount of from 0.01% w/v to 0.03% w/v. In some such compositions, the EDTA is present therein in an amount from 0.05% w/v to 0.15% w/v.

In some compositions of the present disclosure, the ionic tonicity agent is sodium chloride, the buffer is the combination of dibasic sodium phosphate and citric acid; and the pH adjusting agent is hydrochloric acid. In some such compositions, the bimatoprost is present therein in the amount of 0.01% w/v, the EDTA is present therein in the amount of 0.1% w/v, the sodium chloride is present therein in an amount of from 0.75% w/v to 0.85%; the dibasic sodium phosphate is present therein in an amount of from 0.25% w/v to 0.275% w/v; and the citric acid is present therein in an amount of from 0.0125% w/v to 0.175% w/v. Such compositions further have a pH of from 6 to 8.

In some embodiments of the present disclosure, the composition is free of added boric acid.

The present disclosure also provides methods of treating an ophthalmic condition in a patient which involve the topical administration, to ocular tissue of the patient, an amount of a composition of the disclosure that is therapeutically effective to lower intraocular pressure, reduce hyperemia, or promote eyelash growth in the patient. In some such methods, the therapeutically effective amount of the composition is from 5 µl to 100 µl thereof. In some such methods, the composition is administered from once daily to eight times per day. In some such methods, the composition is administered from one day to twenty-one consecutive days.

It is an object of this disclosure to provide aqueous, pharmaceutical compositions, suitable for topical-ophthalmic administration to the eye of a mammal (e.g., a human), that comprise a prostaglandin (e.g., bimatoprost) and no benzalkonium chloride and that provide concentrations of bimatoprost and/or bimatoprost acid in the aqueous humor therapeutically effective to reduce intraocular pressure, reduce ocular hyperemia, and/or or promote eyelash growth in the mammal. Such compositions further comprise EDTA, EGTA, EDDS, or combinations thereof in amounts promoting their function as a penetration enhancer for the prostaglandin (e.g., bimatoprost) across ocular tissue (e.g., corneal epithelium) into the aqueous humor and/or non-deacetylated xanthan gum in amounts promoting its function as a demulcent in ocular tissue. It is a further object of this disclosure to provide such compositions that, simultaneously with achieving the state therapeutic effect(s), induce fewer and/or less severe adverse effects than compositions comprising bimatoprost and benzalkonium chloride.

These and other embodiments are described in further detail below. The detailed description and examples provided herewith depict various embodiments of this disclosure for purposes of illustration only. One skilled in the art will readily recognize from the following discussion that alternative embodiments of the structures and methods illustrated herein may be employed without departing from the principles of embodiments described herein.

DETAILED DESCRIPTION

The present disclosure provides aqueous, pharmaceutical compositions that are suitable for topical, ophthalmic administration and that comprise a prostaglandin, such as bimatoprost latanoprost, tafluprost, travoprost, unoprostone, or a combination thereof and an ocular tissue penetration enhancer, such as EDTA, EGTA, EDDS, or a combination thereof. Certain compositions of the disclosure are useful for reducing, or preventing, elevated levels of TOP in a mammalian subject, such as a human. Certain compositions of the disclosure are useful for reducing, or preventing, hyperemia in such subject. Certain compositions of the disclosure are useful in promoting the growth of eyelashes in such subjects. Certain compositions of the disclosure are useful in more than one of the preceding applications.

The present disclosure is based in part on the inventors' discovery that, pursuant to topical, ocular administration, pharmaceutical compositions consistent with those disclosed herein provide therapeutically effective concentrations, in aqueous humor of a treated eye, of a prostaglandin, such as bimatoprost latanoprost, tafluprost, travoprost, unoprostone, or derivatives thereof, or prodrugs thereof, or pharmaceutically acceptable salts thereof, and combinations thereof. The present inventors have discovered that EDTA, EGTA, EDDS, or combination thereof unexpectedly function as a penetration enhancer in ocular tissues for prostaglandins. The present inventors have further discovered that EDTA, EGTA, EDDS, or combination thereof unexpectedly function as a penetration enhancer in ocular tissues for prostaglandins at relatively lower concentrations in topical-ophthalmic pharmaceutical compositions of the disclosure and as a penetration inhibitor in ocular tissues for prostaglandins at relatively higher concentrations in topical-ophthalmic pharmaceutical compositions.

By way of non-limiting example, in the context of topical-ocular pharmaceutical compositions, EDTA has been observed to enhance or inhibit the penetration of active pharmaceutical ingredients across ocular tissue. (See, e.g., S Piscena et al., *Eur J Pharm Biopharm* 2016, 107:171-179 teaching that EDTA did not enhance the trans-corneal diffusion of cysteamine at pH 7.4 or at pH 4.2, while benzalkonium chloride (BAC) significantly enhanced it; also see S Thakral and M Ahuj a, *J Pharm Negative Results* 2011, 2:24-7 teaching that the use of EDTA as chelating agent in fluconazole ophthalmic solutions significantly decreased the corneal penetration of fluconazole; see also G Roy et al. *Investig Ophthalmol Vis Sci* 1985, 26:110-13 teaching that EDTA increased the corneal penetration of glycerol and cromolyn; see also Mahaling and Katti, Int. J. Pharm. 2016, 501, 1-9 teaching that the use of EDTA decreased the bioavailability of nanoparticles in the lens and choroid; see also WO2021/084522 teaching that the histogram of its FIG. 4 shows the addition of EDTA to the formulation containing 0.01% bimatoprost, poloxamer 188 0.01%, and BAK 50 determines an apparent trans-corneal permeability of corneal cell cultures value similar to that calculated for 0.01% bimatoprost, poloxamer 188 0.01%, and BAK 50 in the absence of EDTA.)

The present inventors further unexpectedly found that, in direct contradiction to the teachings of the prior art, certain compositions described herein unexpectedly exhibited excellent storage stability properties in regards of viscosity despite comprising significant amounts of non-deacetylated ionic polymer xanthan gum.

Prostaglandins. Compositions of the present disclosure comprise one or more of bimatoprost, latanoprost, tafluprost, travoprost, and/or unoprostone, including derivatives thereof, pharmaceutically acceptable salts thereof, and prodrugs thereof. In some embodiments, the prostaglandin has a purity of at least 90%, for example about 90%, about 91%, about 92%, about 93%, about 94%, about 95%, about 96%, about 97%, about 98%, about 99%, or greater than 99%.

Prostaglandins, e.g., bimatoprost, latanoprost, tafluprost, travoprost, and/or unoprostone may be present in compositions consistent with the present disclosure in an amount sufficient to treat a condition such as elevated TOP, ocular hypertension, glaucoma (e.g., open angle glaucoma), or hypotrichosis of the eyelashes. In some embodiments, such prostaglandin/s is/are present in a composition of the present disclosure in an amount of about 0.005% w/v to about 0.05% w/v, or about 0.01% w/v to about 0.03% w/v, for example about 0.005% w/v, about 0.006% w/v, about 0.007% w/v, about 0.008% w/v, about 0.009% w/v, about 0.01% w/v, about 0.011% w/v, about 0.012% w/v, about 0.013% w/v, about 0.014% w/v, about 0.015% w/v, about 0.016% w/v, about 0.017% w/v, about 0.018% w/v, about 0.019% w/v, about 0.02% w/v, about 0.021% w/v, about 0.022% w/v, about 0.023% w/v, about 0.024% w/v, about 0.025% w/v, about 0.026% w/v, about 0.027% w/v, about 0.028% w/v, about 0.029% w/v, about 0.03% w/v, about 0.031% w/v, about 0.032% w/v, about 0.033% w/v, about 0.034% w/v, about 0.035% w/v, about 0.036% w/v, about 0.037% w/v, about 0.038% w/v, about 0.039% w/v, about 0.04% w/v, about 0.041% w/v, about 0.044% w/v, about 0.043% w/v, about 0.044% w/v, about 0.045% w/v, about 0.046% w/v, about 0.047% w/v, about 0.048% w/v, about 0.049% w/v, about 0.05% w/v. In some embodiments, bimatoprost is present in a composition of the present disclosure in an amount of in an amount of about 0.01% w/v. In some embodiments, bimatoprost is present in a composition of the present disclosure in an amount of in an amount of about 0.03% w/v.

Compositions of the present disclosure may additionally include a penetration enhancer for a prostaglandin, e.g., bimatoprost, latanoprost, tafluprost, travoprost, and/or unoprostone, across ocular tissue (e.g., corneal epithelium). In some embodiments, the penetration enhancer comprises, consists essentially of, or consists of EDTA, EGTA, EDDS, or a combination thereof, preferably EDTA. The penetration enhancer may be present in topical, ophthalmic compositions of the disclosure in amounts effective to increase the quantity prostaglandin that infiltrates the aqueous humor through the cornea following topical, ocular administration of such compositions to a subject. In some embodiments, the penetration enhancer, EDTA, EGTA, EDDS, or combination thereof is present in topical, ophthalmic compositions of the disclosure in an amount of from about 0.1% w/v to less than 0.3% w/v, or from about 0.15% w/v to about 0.25% w/v, for example about 0.1% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.2% w/v, about 0.21% w/v, about 0.22% w/v, about 0.23% w/v, about 0.24% w/v, about 0.25% w/v, about 0.26% w/v, about 0.27% w/v, about 0.28% w/v, or about 0.29% w/v.

The effect of a penetration enhancer may be determined using any method known in the art: e.g., without limitation, side-by-side experiments in which the concentration of a prostaglandin, e.g., bimatoprost, latanoprost, tafluprost, travoprost, and/or unoprostone, or there free acids or derivatives, is assayed in the aqueous humor of a subject after topical, ocular administration of a unit dose of: (i) a composition of the present disclosure that contains bimatoprost and a penetration enhancer, and (ii) a composition that is the same as (i) except that it lacks penetration enhancer.

The penetration enhancers present in the composition of the disclosure may perform additional functions therein, and therefore any particular, multifunctional excipient being identified as a "penetration enhancer" does not limit the scope of the instant disclosure or its appended claims to exclude any its additional non-penetration enhancer functions, unless it is expressly so-recited. For example and without limitation, EDTA may act as both a penetration enhancer and a preservative in compositions of the present disclosure.

Compositions of the present disclosure additionally include a solvent or solvent system. In some embodiments, the solvent comprises, consists essentially of, or consists of water. Compositions of the present disclosure may include additional excipients suitable for use in topical, ophthalmic pharmaceuticals, such as tonicity agents, buffers, polymers, pH adjusting agents, and the like.

Ionic tonicity agents useful in the compositions described herein include calcium chloride, magnesium chloride, potassium chloride, sodium chloride, and sodium sulfate. Non-ionic tonicity agents useful in the composition described herein include propylene glycol, glycerol, mannitol, sorbitol, xylitol, erythritol, lactitol, maltitol, and isomalt. In such embodiments, the compositions may comprise tonicity agent(s) at a concentration of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or ranges between any of said tonicity agent concentrations. The compositions may comprise combinations of tonicity agents, in amounts that individually or in aggregate achieve(s) said tonicity agent concentrations.

In some embodiments, the compositions of the present disclosure may comprise an osmolality of about 250 mOsmol/kg to about 350 mOsmol/kg, or about 275 mOsmol/kg to about 305 mOsmol/kg, for example about 250 mOsmol/kg, about 255 mOsmol/kg, about 260 mOsmol/kg, about 265 mOsmol/kg, about 270 mOsmol/kg, about 275 mOsmol/kg, about 280 mOsmol/kg, about 285 mOsmol/kg, about 290 mOsmol/kg, about 295 mOsmol/kg, about 300 mOsmol/kg, about 305 mOsmol/kg, about 310 mOsmol/kg, about 315 mOsmol/kg, about 320 mOsmol/kg, about 325 mOsmol/kg, about 330 mOsmol/kg, about 335 mOsmol/kg, about 340 mOsmol/kg, about 345 mOsmol/kg, or about 350 mOsmol/kg, or ranges between any of said osmolalities. The formulations may comprise combinations of tonicity agent, in amounts that individually or in aggregate achieve(s) said tonicity agent concentrations and/or said osmolalities.

Buffers useful in the compositions described herein include acetic acid, sodium acetate, adipic acid, benzoic acid, sodium benzoate, boric acid, sodium borate, citric acid, sodium citrate, glycine, maleic acid, sodium phosphate, monobasic sodium phosphate, dibasic sodium phosphate, potassium phosphate, monobasic potassium phosphate, dibasic potassium phosphate, HEPES (N-(2-hydroxyethyl)piperazine-N'-(2-ethanesulfonic acid), lactic acid, tartaric acid, sodium tartrate, sodium bicarbonate, sodium carbonate, and TRIS (tris(hydroxymethyl)aminomethane). In such embodiments, the compositions may comprise buffer(s) at a concentration of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or ranges between any of said tonicity agent concentrations. The compositions may comprise combinations of buffers, in amounts that individually or in aggregate achieve(s) said buffer concentrations.

pH adjusting agents useful in the compositions of the present disclosure include sodium hydroxide, potassium hydroxide, citric acid, and hydrochloric acid. Compositions of the present disclosure may contain amounts of pH adjusting agents sufficient to achieve a pH of about 4 to about 8.5, for example about pH 4, about pH 4.1, about pH 4.2, about pH 4.3, about pH 4.4, about pH 4.5, about pH 4.6, about pH 4.7, about pH 4.8, about pH 4.9, about pH 5, about pH 5.1, about pH 5.2, about pH 5.3, about pH 5.4, about pH 5.5, about pH 5.6, about pH 5.7, about pH 5.8, about pH 5.9, about pH 6, about pH 6.1, about pH 6.2, about pH 6.3, about pH 6.4, about pH 6.5, about pH 6.6, about pH 6.7, about pH 6.8, about pH 6.9, about pH 7, about pH 7.1, about pH 7.2, about pH 7.3, about pH 7.4, about pH 7.5, about pH 7.6, about pH 7.7, about pH 7.8, about pH 7.9, about 8, about pH 8.1, about pH 8.2, about pH 8.3, about pH 8.4, or about pH 8.5.

Nonionic polymers useful in the compositions of the disclosure include polyethylene glycol, hydroxyethyl cellulose, hydroxypropylmethyl cellulose, methyl cellulose, carboxymethyl cellulose, polyvinyl pyrrolidone, and polyvinyl alcohol. Ionic polymers useful in the compositions of the disclosure include polyacrylates (e.g., carbopols and carbomers), alginates, chitosans, hyaluronic acid, and xanthan gum. In such embodiments, the compositions may comprise polymers at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said polymer concentrations. The compositions may comprise combinations of polymers, in amounts that individually or in aggregate achieve(s) the stated polymer concentrations.

In some embodiments, the topical-ophthalmic compositions described herein exhibit storage stability in regards of viscosity. In such embodiments, the formulation maintains a viscosity of at least 60%, at least 70%, at least 80%, at least 90%, at least 95%, at least 97%, or at least 99% of its initial viscosity after storage for one, two, three, four, eight, or sixteen weeks, at 40° C., 50° C., or 60° C. The initial viscosity of the formulation is measured within a period of not more than 24 hours post manufacture in which the temperature is maintained between 4° C. and 30° C. The initial and storage viscosities are determined with the viscosity assay described in Example 2. Such formulations are referred to as, respectively, 60%, 70%, 80%, 90%, 95%, 97%, or 99% viscosity stable for one, two, four, eight, or sixteen weeks, at 40° C., 50° C., or 60° C.

In some embodiments, compositions of the present disclosure do not include benzalkonium chloride. In some embodiments, the compositions are free of added: (i) benzalkonium chloride, and (ii) poloxamer. In some embodiments, the compositions are free of added: (i) benzalkonium chloride, (ii) poloxamer, and/or (iii) polysorbate. In some embodiments, compositions of the present disclosure are sterilized, by any means known in the art.

Some specific exemplary formulations consistent with the present disclosure are summarized below in Table A.

TABLE A

Exemplary Benzalkonium Chloride-Free Bimatoprost Formulations

| Ex. | Bimatoprost | EDTA | BAK[1] | NaCl | Buffer System | pH Adjuster(s) | Solvent |
|---|---|---|---|---|---|---|---|
| 1 | 0.01% w/v | 0.05% w/v | 0 | 8.1 mg/mL | A[2] | HCl/NaOH to pH 6-8 | Purified water |
| 2 | 0.01% w/v | 0.1% w/v | 0 | 8.1 mg/mL | A | HCl/NaOH to pH 6-8 | Purified water |
| 3 | 0.01% w/v | 0.15% w/v | 0 | 8.1 mg/mL | A | HCl/NaOH to pH 6-8 | Purified water |
| 4 | 0.01% w/v | 0.2% w/v | 0 | 8.1 mg/mL | A | HCl/NaOH to pH 6-8 | Purified water |
| 5 | 0.01% w/v | 0.25% w/v | 0 | 8.1 mg/mL | A | HCl/NaOH to pH 6-8 | Purified water |
| 6 | 0.02% w/v | 0.05% w/v | 0 | 8.1 mg/mL | A | HCl/NaOH to pH 6-8 | Purified water |
| 7 | 0.02% w/v | 0.1% w/v | 0 | 8.1 mg/mL | A | HCl/NaOH to pH 6-8 | Purified water |
| 8 | 0.02% w/v | 0.15% w/v | 0 | 8.1 mg/mL | A | HCl/NaOH to pH 6-8 | Purified water |
| 9 | 0.02% w/v | 0.2% w/v | 0 | 8.1 mg/mL | A | HCl/NaOH to pH 6-8 | Purified water |
| 10 | 0.02% w/v | 0.25% w/v | 0 | 8.1 mg/mL | A | HCl/NaOH to pH 6-8 | Purified water |
| 11 | 0.03% w/v | 0.05% w/v | 0 | 8.1 mg/mL | A | HCl/NaOH to pH 6-8 | Purified water |
| 12 | 0.03% w/v | 0.1% w/v | 0 | 8.1 mg/mL | A | HCl/NaOH to pH 6-8 | Purified water |
| 13 | 0.03% w/v | 0.15% w/v | 0 | 8.1 mg/mL | A | HCl/NaOH to pH 6-8 | Purified water |
| 14 | 0.03% w/v | 0.2% w/v | 0 | 8.1 mg/mL | A | HCl/NaOH to pH 6-8 | Purified water |
| 15 | 0.03% w/v | 0.25% w/v | 0 | 8.1 mg/mL | A | HCl/NaOH to pH 6-8 | Purified water |

[1]BAK = Benzalkonium chloride
[2]Buffer system A = 0.268% w/v dibasic sodium phosphate heptahydrate and 0.014% w/v citric acid monohydrate Methods of Making Pharmaceutical Compositions Comprising Bimatoprost. The present disclosure further provides methods of making compositions comprising a prostaglandin. In some embodiments, a method of making a pharmaceutical composition comprising a prostaglandin (e.g., bimatoprost, latanoprost, tafluprost, travoprost, and/or unoprostone, including derivatives thereof, pharmaceutically acceptable salts thereof, and prodrugs thereof) consistent with the present disclosure comprises combining bimatoprost and EDTA in water to form a prostaglandin solution. In some embodiments, the method further comprises sterilizing the prostaglandin solution (e.g., by overkill method or by membrane filtration) to produce a pharmaceutical composition comprising prostaglandin. In some embodiments, the step of combining prostaglandin and EDTA further comprises combining prostaglandin, EDTA, a buffer system (e.g., dibasic sodium phosphate heptahydrate and citric acid monohydrate), and a tonicity agent (e.g., sodium chloride) in purified water to produce the bimatoprost solution. In some embodiments, the method further comprises adjusting the pH of the prostaglandin solution to pH 6-8 by, for example, contacting the bimatoprost solution with sodium hydroxide and/or hydrochloric acid until the prostaglandin solution has a pH of 6-8. In some embodiments, the method further comprises placing the prostaglandin solution in a container before a step of sterilizing the prostaglandin solution. In some embodiments, the method further comprises filtering the prostaglandin solution through a membrane filter (e.g., a 0.22 μm membrane filter or similar) into a container. In some embodiments, the method further comprises sanitizing the container before filtering the prostaglandin solution into the container. In some embodiments, the method does not include a step of combining a quaternary ammonium salt with the prostaglandin or a solution comprising prostaglandin. In some embodiments, the method does not include a step of combining benzalkonium chloride with the prostaglandin or a solution comprising prostaglandin.

EXAMPLES

Aspects of embodiments may be further understood in light of the following examples, which should not be construed as limiting in any way.

Example 1

Penetration Study. The objective of this penetration study is to evaluate aqueous humor concentrations of bimatoprost and bimatoprost acid following a single ocular instillation of bimatoprost 0.01% in female New Zealand white rabbits. A single aliquot of 28 μL of the assigned formulation was instilled in each eye (bilaterally) for animals in all groups. Test formulations A-D were prepared with the compositions specified in Table 1.1.

TABLE 1.1

| Test Formulations | | | |
|---|---|---|---|
| Test Formulation | Test A | Test B | Test C |
| Batch No. | C024-227-54A | C024-227-54B | C024-227-54C |
| Bimatoprost | 0.01% w/v | 0.01% w/v | 0.01% w/v |
| Sodium Chloride | 0.81% w/v | 0.81% w/v | 0.81% w/v |
| Dibasic Sodium Phosphate | 0.268% | 0.268% | 0.268% |
| Citric Acid Monohydrate | 0.014% | 0.014% | 0.014% |

TABLE 1.1-continued

| Test Formulations | | | |
|---|---|---|---|
| Test Formulation | Test A | Test B | Test C |
| Benzalkonium chloride | 0 | 0 | 0 |
| EDTA | 0.3% w/v | 0.1% w/v | 0 |
| Hydrochloric Acid to pH: 7.3 | q.s. | q.s. | q.s. |
| Purified Water | q.s. | q.s. | q.s. |
| Assay (bimatoprost) | 101.9% | 101.9% | 101.9% |
| Storage conditions | Refrigerated | Refrigerated | Refrigerated |

Each Test Formulation A, B, and C was stored in amber glass bottles at 2-8° C. until 8-24 hours before dosing. Prior to dosing, each Test Formulation was allowed to equilibrate to room temperature. Tests were conducted on female New Zealand White Rabbits (*Oryctolagus cuniculus*) aged 4-8 months. Animals were randomized by the zig-zag method to provide n=3 per Test Formulation and housed at 20° C.+/−3° C. with a photoperiod of 12 hours light/12 hours dark and a minimum of 12 fresh HEPA-filtered air changes per hour. At randomization, each animal's weight was +/−20% of the mean weight within each group and across all groups.

Each animal was dosed with 56 μL of the assigned Test Formulation (28 μL per eye), with each animal being dosed in both eyes within 5 minutes or less. Sixty minutes after dosing, each animal was euthanized by overdose of sodium thiopentene solution. Both eyes of each animal were washed with normal saline and blotted dried with tissue paper. Aqueous humor from both eyes were collected (approx. 150 μL per eye) from the anterior chamber of each eye using 1 mL of tuberculin syringe connected with a needle. Left and right eye samples were stored in separate vials. Post collection, each sample was stored immediately on crushed ice followed by storage at −20+/−3° C. within 15 minutes of sample collection. Post completion of in-life phase all samples of aqueous humor was transferred to storage at −70+/−10° C. Bimatoprost concentrations in aqueous humor were determined by LC-MS/MS using the parameters specified in Table 1.2.

TABLE 1.2

| Chromatographic Parameters Bimatoprost Assay | | | |
|---|---|---|---|
| HPLC | Nexera X2 | | |
| Mass Spec | API 4000 QTrap | | |
| Polarity | Positive ion mode | | |
| Ion source | Electron ion spray | | |
| Column | BDS Hypersil C18, 100 × 4.6 mm, 3.5 μm | | |
| Oven temperature | 45° C. | | |
| Peltier temperature | 15° C. | | |
| Mobile phases | A: 0.1% Formic acid in water B: 0.1% Formic acid in acetonitrile | | |
| Flow rate | 0.900 mL/min | | |
| Mobile phase gradient | t = 0.00 min | 55% A | 45% B |
| | t = 0.30 min | 55% A | 45% B |
| | t = 1.00 min | 10% A | 90% B |
| | t = 2.70 min | 10% A | 90% B |
| | t = 2.71 min | 55% A | 45% B |
| | t = 4.00 min | 55% A | 45% B |
| Injection volume | 15 μL | | |
| Run time | 4.00 min | | |
| Retention times | Bimatoprost: 2.59 +/− 0.5 minutes Carbamazepine (ISTD) 2.56 +/− 0.5 minutes | | |

TABLE 1.2-continued

Chromatographic Parameters Bimatoprost Assay

| | |
|---|---|
| Detection ions | Bimatoprost: 416.100 amu (parent), 362.100 amu (product) |
| | Carbamazepine: 237.000 amu (parent), 194.000 amu (product) |
| MRM Conditions | |
| Temperature | 550° C. |
| Ion spray voltage | 5500 |
| Curtain gas | 25 psi |
| CAD gas | 6 psi |
| Gas 1 | 45 psi |
| Gas 2 | 55 psi |
| Declustering potential | Bimatoprost: 42 |
| | Carbamazepine: 75 |
| Collision energy | Bimatoprost: 16 |
| | Carbamazepine: 52 |
| Collision cell exit potential | Bimatoprost: 11 |
| | Carbamazepine: 12 |
| Entrance potential | Bimatoprost: 10 |
| | Carbamazepine: 10 |

Chromatography procedure (bimatoprost assay). Blank plasma was retrieved from the deep freezer and allowed to thaw. Calibration Curve Standard and Quality Control were spiked in plasma. Carbamazepine (5 μL a 100 ng/mL) was added to all samples except plasma blank. Blank plasma (50 μL) was added to two radioimmunoassay (RIA) vials labeled as Plasma blank and Plasma blank+ISTD. Sample (50 μL) was transferred to the RIA vials from the corresponding samples and vortex mixed. Formic acid (0.150 mL of 0.1% in acetonitrile) was added to all samples and samples were kept on the shaker for 5 min to ensure complete mixing of contents. Each sample was centrifuged at 4000 rpm and 20° C. for 5 minutes. The supernatant layer was transferred into RIA vials and loaded the into auto sampler vials. Bimatoprost concentrations in aqueous humor were determined by LC-MS/MS using the parameters specified in Table 1.3.

TABLE 1.3

Chromatographic Parameters Bimatoprost Acid Assay

| | | | |
|---|---|---|---|
| HPLC | Nexera X2 | | |
| Mass Spec | API 4000 QTrap | | |
| Polarity | Negative ion mode | | |
| Ion source | Electron ion spray | | |
| Column | BDS Hypersil C18, 100 × 4.6 mm, 3.5 μm | | |
| Oven temperature | 45° C. | | |
| Peltier temperature | 15° C. | | |
| Mobile phases | A: 0.1% Formic acid in water | | |
| | B: 0.1% Formic acid in acetonitrile | | |
| Flow rate | 0.900 mL/min | | |
| Mobile phase gradient | t = 0.00 min | 55% A | 45% B |
| | t = 0.30 min | 55% A | 45% B |
| | t = 1.00 min | 10% A | 90% B |
| | t = 2.70 min | 10% A | 90% B |
| | t = 2.71 min | 55% A | 45% B |
| | t = 4.00 min | 55% A | 45% B |
| Injection volume | 15 μL | | |
| Run time | 4.00 min | | |
| Retention times | Bimatoprost acid: 2.60 +/− 0.5 minutes | | |
| | Travoprost acid (ISTD) 2.90 +/− 0.5 minutes | | |
| Detection ions | Bimatoprost acid: 387.401 amu (parent), 343.100 amu (product) | | |
| | Travoprost acid: 457.100 amu (parent), 161.300 amu (product) | | |
| MRM Conditions | | | |
| Temperature | 550° C. | | |
| Ion spray voltage | −4500 | | |

TABLE 1.3-continued

Chromatographic Parameters Bimatoprost Acid Assay

| | |
|---|---|
| Curtain gas | 25 psi |
| CAD gas | 6 psi |
| Gas 1 | 50 psi |
| Gas 2 | 55 psi |
| Declustering potential | Bimatoprost acid: −88 |
| | Travoprost acid: −55 |
| Collision energy | Bimatoprost acid: −35 |
| | Travoprost acid: −46 |
| Collision cell exit potential | Bimatoprost acid: −15 |
| | Travoprost acid: −10 |
| Entrance potential | Bimatoprost acid: −10 |
| | Travoprost acid: −10 |

TABLE 1.4

Penetration Study Results
Aqueous Humor Concentration (ng/mL)

| Formulation | Bimatoprost Acid (left and right eye mean) |
|---|---|
| Test A (n = 6) | 4.19 |
| Test B (n = 6) | 5.45 |
| Test C (n = 6) | 4.26 |

These results demonstrate that EDTA surprisingly functions, in a concentration-dependent manner, as both a penetration enhancer and a penetration inhibitor, for bimatoprost through corneal tissues into the aqueous humor.

Example 2

Viscosity Assay. The viscosity of pharmaceutical, topical-ophthalmic compositions of the present disclosure may be determined using a Malvern Kinexus Rheometer. Each viscosity measurement tests a 0.5 mL sample and runs a shear rate ramp to determine the viscosity flow curve of the sample at different shear rates. A software algorithm evaluates the resulting data, and a data point was taken when the shear rate reaches an equilibrium value. The viscosity flow curve test parameters set forth in Table 2.1 are applied to all samples.

TABLE 2.1

Viscosity Flow Curve Test Parameters

| | |
|---|---|
| Gap | 0.05 mm |
| Temperature | 25° C. |
| Start shear rate | 0.01 (1/sec) |
| End shear rate | 10,000 (1/sec) |
| Upper geometry | CP 1/100 |

Pharmaceutical, topical-ophthalmic compositions having the ingredients set forth in Table 2.2, of which the xanthan gum is not deacetylated, are studied in the viscosity assay. Pharmaceutical, topical-ophthalmic compositions of the present disclosure are viscosity stable.

TABLE 2.2

| Composition | I | II | II |
|---|---|---|---|
| Bimatoprost | 0.01% w/v | 0.01% w/v | 0.01% w/v |
| Sodium Chloride | 0.81% w/v | 0.81% w/v | 0.81% w/v |

TABLE 2.2-continued

| Composition | I | II | II |
|---|---|---|---|
| Dibasic Sodium Phosphate | 0.268% | 0.268% | 0.268% |
| Citric Acid Monohydrate | 0.014% | 0.014% | 0.014% |
| EDTA | 0.1% w/v | 0.1% w/v | 0.1% w/v |
| Xanthan Gum | 0.60 w/v % | 0.30 w/v % | 0.10 w/v % |
| Hydrochloric Acid to pH: 7.3 | q.s. | q.s. | q.s. |
| Purified Water | q.s. | q.s. | q.s. |
| Assay (bimatoprost) | 101.9% | 101.9% | 101.9% |
| Storage conditions | Refrigerated | Refrigerated | Refrigerated |

It is surprisingly found that, despite containing xanthan gum that is not deacetylated, the formulations demonstrated excellent viscosity stability properties.

What is claimed is:

1. An aqueous pharmaceutical composition comprising:
   from 0.001% w/v to 2% w/v of a prostaglandin that is a bimatoprost, a latanoprost, a tafluprost, a travoprost, a unoprostone, a derivative thereof, or a combination thereof;
   from 0.0025% w/v to about 0.1% w/v of an ocular tissue penetration enhancer that is an ethylenediaminetetraacetic acid ("EDTA"), an ethylene glycol tetraacetic acid ("EGTA"), an ethylenediamine-N,N'-disuccinic acid ("EDDS"), or a combination thereof;
   from 0.001% w/v to 2% w/v of an ionic tonicity agent that is a calcium chloride, a magnesium chloride, a potassium chloride, a sodium chloride, a sodium sulfate, or a combination thereof;
   a viscosity of from 1 centipoise ("cps") to 8000 cps; and water,
   wherein the composition is free of added: (i) benzalkonium chloride, and (ii) poloxamer.

2. The composition of claim 1, further comprising:
   a buffer that is a tris(hydroxymethyl)aminomethane ("TRIS"), an acetic acid, a sodium acetate, a benzoic acid, a sodium benzoate, a boric acid, a sodium borate, a citric acid, a sodium citrate, a sodium phosphate, a monobasic sodium phosphate, a dibasic sodium phosphate, a potassium phosphate, a monobasic potassium phosphate, a dibasic potassium phosphate, a sodium acetate, a lactic acid, a tartaric acid, a sodium tartrate, a sodium bicarbonate, a sodium carbonate, or a combination thereof;
   a pH adjusting agent that is a sodium hydroxide, a potassium hydroxide, a citric acid, a hydrochloric acid, or a combination thereof,
   wherein the buffer and pH adjusting agent are present in the composition in amounts that result in the composition having a pH of from 5 to 9.

3. The composition of claim 2, wherein:
   the prostaglandin is bimatoprost; and
   the penetration enhancer is the EDTA.

4. The composition of claim 3, wherein the composition comprises:
   from 0.01% w/v to 0.03% w/v of bimatoprost; and
   from 0.05% w/v to about 0.1% w/v of EDTA.

5. The composition of claim 4, wherein:
   the ionic tonicity agent is sodium chloride;
   the buffer is the combination of dibasic sodium phosphate and citric acid; and
   the pH adjusting agent is hydrochloric acid.

6. The composition of claim 5, wherein the composition comprises:
   0.01% w/v of bimatoprost;
   0.1% w/v of EDTA;
   from 0.75% w/v to 0.85% w/v of sodium chloride;
   from 0.25% w/v to 0.275% w/v of dibasic sodium phosphate; and
   from 0.0125% w/v to 0.175% w/v of citric acid; and
   wherein the composition has a pH of from 6 to 8.

7. A method of treating an ophthalmic condition in a patient in need thereof, said method comprising topically administering to an eye of the patient an amount of the composition of claim 1 that is therapeutically effective in lowering intraocular pressure or hyperemia, or promoting eyelash growth, in the patient.

8. The method of claim 7, wherein the therapeutically effective amount of the composition is from 5 µl to 100 µl thereof.

9. The method of claim 8, wherein the composition is administered from once daily to eight times per day.

10. The method of claim 9, wherein the composition is administered from one to twenty-one consecutive days.

* * * * *